United States Patent [19]
Quinlan

[11] Patent Number: 5,209,679
[45] Date of Patent: May 11, 1993

[54] ADAPTIVE MEDICAL ELECTRODE CONNECTOR WITH MALE STUD

[75] Inventor: Donald P. Quinlan, Orchard Park, N.Y.

[73] Assignee: Graphic Controls Corporation, Buffalo, N.Y.

[21] Appl. No.: 884,613

[22] Filed: May 15, 1992

Related U.S. Application Data

[63] Continuation of Ser. No. 749,543, Aug. 23, 1991, abandoned.

[51] Int. Cl.$^5$ .................................... H01R 4/48
[52] U.S. Cl. ........................ 439/822; 439/909; 128/639
[58] Field of Search ............... 128/639–641, 128/798, 802; 439/217, 218, 224, 504, 506, 822, 829, 907, 909, 912

[56] References Cited

U.S. PATENT DOCUMENTS

| | | | |
|---|---|---|---|
| 2,611,368 | 9/1952 | Pecora | 128/639 |
| 2,644,142 | 6/1953 | Danberg | 439/224 |
| 3,606,881 | 9/1971 | Woodson | 128/206 E |
| 3,829,826 | 8/1974 | Brown et al. | 24/218 |
| 3,850,490 | 11/1974 | Zehr | 439/882 |
| 4,094,571 | 6/1978 | Benjamin | 128/416 |
| 4,126,126 | 11/1978 | Bare et al. | 128/206 E |
| 4,178,052 | 12/1979 | Ekbom et al. | |
| 4,209,020 | 6/1980 | Nielsen | 128/640 |
| 4,268,101 | 5/1981 | Stone | 24/110 |
| 4,332,257 | 6/1982 | Ayer | 128/640 |
| 4,490,005 | 12/1984 | Hovey | 128/641 |
| 4,637,672 | 1/1987 | Peterman et al. | 128/639 |
| 4,640,563 | 2/1987 | LeBlanc | 439/217 |
| 4,653,500 | 3/1987 | Osada et al. | 128/639 |
| 4,671,591 | 6/1987 | Archer | 439/346 |
| 4,685,467 | 8/1987 | Cartmell et al. | 128/640 |
| 4,700,997 | 10/1987 | Strand | 439/372 |
| 4,702,256 | 10/1987 | Robinson et al. | 128/639 |
| 4,721,111 | 1/1988 | Muttitt | 128/640 |
| 4,797,125 | 1/1989 | Malana | 439/729 |
| 4,832,608 | 5/1989 | Kroll | 439/67 |
| 4,865,566 | 9/1989 | Rasmussen | 439/825 |
| 4,904,205 | 2/1990 | Rice | 439/504 |
| 4,911,657 | 3/1990 | Bertin | 439/502 |
| 4,938,219 | 4/1990 | Ishii et al. | 128/641 |
| 4,938,712 | 7/1990 | Black | 439/504 |
| 4,945,911 | 8/1990 | Cohen et al. | 128/640 |
| 5,024,620 | 6/1991 | Bell | 439/829 |

Primary Examiner—Gary F. Paumen
Attorney, Agent, or Firm—Ratner & Prestia

[57] ABSTRACT

An electrical conducting connector used to interconnect medical electrodes and monitoring devices. The male stud, commonly manufactured on the electrode, is relocated to a new position as an integral part of the connector. Consequently, the connector can act as an adapter for electrically interconnecting a relatively inexpensive, flexible, studless electrode secured on the skin of a patient to a monitor having a conventional lead wire plus female couple assembly. Such interconnection allows rotation between the connector and electrode, thereby assuring patient comfort and continued electrical contact even when the electrode is adhered to the patient for long periods of monitoring.

6 Claims, 2 Drawing Sheets

ADAPTIVE MEDICAL ELECTRODE CONNECTOR WITH MALE STUD

This application is a continuation of application Ser. No. 07/749,543 filed Aug. 23, 1991, now abandoned.

BACKGROUND OF THE INVENTION

1. Field of the Invention

The present invention relates to biomedical electrodes of the type attached to the body and, more particularly, to an adaptive electrical connector which permits a conventional lead wire plus female couple assembly to interconnect a studless electrode by locating an electrode stud on the connector.

2. Background of the Invention

Various configurations exist for electrical conducting connectors such as those used to interconnect electrodes, for example medical or biomedical electrodes, to their corresponding leads and, in turn, monitors. The field is relatively crowded. Designs are usually controlled by, first, a requirement for a secure fastening of the connector to an electrode because the electrode may be part of a life support system. A second requirement of a connector design is controlled by economics: the connector must be easily disposable and replaceable (hence, inexpensively manufactured) to maintain sterility in a medical environment.

Perhaps the most common type of connector simply consists of a quick disconnect, female couple at one end of a lead wire. The couple is designed to hook, snap, or otherwise engage a male stud placed on the electrode to make electrical contact with that electrode. The hook or snap operation of the female couple-stud assembly is advantageous because it gives the operator (e.g., a nurse) affirmative assurance that connection to the electrode has been made; engagement creates a noticeable feel and, typically, an audible sound.

This type of connector is especially desirable for medical electrodes because it allows the electrode to be positioned on the patient and then easily connected or disconnected from its corresponding lead. For that reason, most monitors used by hospitals and clinics incorporate leads which have female couples. Moreover, the quick disconnect capability is advantageous especially for disposable electrodes; such electrodes are discarded after use and a single lead is reused with a number of electrodes. The lead wire plus female couple connector requires, however, that the electrode which it engages have a conductive male stud.

Another common type of connector is able to engage a studless electrode. One example of such a connector includes two, pivotally mounted, spring-biased metal jaws which may have multiple teeth for gripping the electrode: an alligator clip. Another example is disclosed in U.S. Pat. No. 4,702,256 issued to Robinson et al.

The electrical connector disclosed by Robinson et al. offers a unique gripping surface which allows the connector to maintain a good grip on a studless electrode without piercing it. A small, plastic member is provided with an electrical contact mounted in one of its jaws. The contact mates with an angled edge on the opposite jaw of the member to crimp and securely grip a studless electrode in the connector while making good electrical contact.

Still other types of connectors able to engage a studless electrode are disclosed, for example, in U.S. Pat. No. 4,797,125 issued to Malana and U.S. Pat. No. 4,178,052 issued to Ekbom et al.

The electrodes to which these various electrical conducting connectors attach can generally be placed into two categories. In one category are those electrodes which have a male stud. The connector interconnects the "stud-containing" electrode by engaging the stud. An advantage of such an electrode is that it permits rotation between the electrode and the connector. Rotation both assures patient comfort and prevents the electrode from disengaging when the patient moves.

The other type of electrode is usually thin, flat, flexible, disposable, studless, and, therefore, less expensive to manufacture or use. The connector interconnects that second type of electrode by engaging the electrode itself, usually at a lateral extension or tab. Thus, this second type of electrode is referred to as a "tab" electrode.

One problem with the tab electrode is that it typically does not permit rotation between the electrode and the connector. Another problem is that tab electrodes cannot be readily connected to the female couple connector of the type in wide-spread use for making contact with the stud-containing electrodes. Consequently, many hospitals and clinics cannot benefit from the cost savings provided by the tab electrodes.

The general object of the present invention is, therefore, to provide an electrode connector which functions as an adapter and allows such facilities to use the advantageous (e.g., inexpensive) tab-type electrode with their conventional monitor-lead-female couple assemblies—while allowing rotation between the connector and electrode. Such a connector assures that each of the electrodes and connectors described above can be interconnected.

In order to achieve that general object, a more specific object is to place a male stud on the electrically conducting connector. A connector with a male stud eliminates the need for the electrode to carry the stud. Thus, the stud can be removed from the electrode and studless, tab-type electrodes, with all of their benefits—primarily reduced cost both to manufacture and to use—can be applied. Such application is feasible even with conventional lead wire plus female couple connectors and retains an important advantage of the stud-containing electrodes, namely, rotation between the connector and electrode.

Patient comfort is the overriding concern with any electrode and connector design. Accordingly, it is an object of the present invention to assure patient comfort. At the same time, rotational movement between the connector and electrode may be necessary to provide a good electrical connection. Such connection must be assured even when the patient moves. Accordingly, it is another object of the present invention to assure significant rotational movement between the connector and the electrode.

The Lec Tec Corporation has developed one design which removes the male stud from an electrode (see U.S. Pat. No. 4,911,657 issued to Berlin). As with many of the patented devices which remove the stud from the electrode, however, the Lec Tec design requires additional, non-standard, non-disposable, costly equipment. Moreover, it is not adapted to use the standard and conventional lead wire plus female couple assemblies now in widespread use; rather, it replaces those assemblies.

Specifically, the biomedical electrode connector disclosed in the patent has a lead wire with a female couple connector at one end and, adjacent to that connector, a male stud which is secured to the lead wire by a tether. The male stud and female couple are aligned on opposite sides of a tab portion of a tab-type electrode. They establish both a mechanical and an electrical connection to the tab when snapped together through the tab.

The focus of the Lec Tec design is to enable a separate lead wire provided with a female couple connector to be used with tab-type electrodes. The design works best when the electrode has a pre-punched opening in its tab to allow the male and female members of the connector to engage. Absent such an opening, the connector must be forced together to puncture the tab before the male and female members engage. The requirement of force is undesirable. Further objects of the present invention are to avoid the need either for a pre-punched hole in the electrode or the use of force to create a hole in the electrode.

Moreover, the focus of the Lec Tec design on tab-type electrodes makes it less desirable for stud-containing electrodes. When the female member of the connector is used to engage the male stud on the stud-containing electrode, the tethered male member of the connector is unnecessary. It dangles uselessly, therefore, as an undesirable potential obstruction. Another object of the present invention is to avoid potentially obstructing structure.

A further object is to avoid unnecessary replacement of the conventional lead wire plus female couple assemblies connected to most monitors. Consider, for example, a monitor having a conventional assembly interconnected to a first patient with a stud-containing electrode in place. In order to use the Lec Tec design with that monitor for a second patient with a tab-type electrode in place, the conventional assembly must be disconnected and the Lec Tec design inserted into the monitor. In contrast, the present design adapts the conventional assembly for use with the second patient without disconnecting that assembly from the monitor.

SUMMARY OF THE INVENTION

To achieve these and other objects, and in view of its purposes, the present invention provides an electrical conducting connector used to interconnect electrodes and monitoring devices. The invention relocates the male stud, commonly manufactured on the electrode, to a new position as an integral part of the connector. Consequently, the connector can act as an adapter for electrically interconnecting a flexible, studless electrode secured on the skin of a patient to a monitor having a conventional lead wire plus female couple assembly.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing, in which.

DETAILED DESCRIPTION OF THE INVENTION

Figure 1:
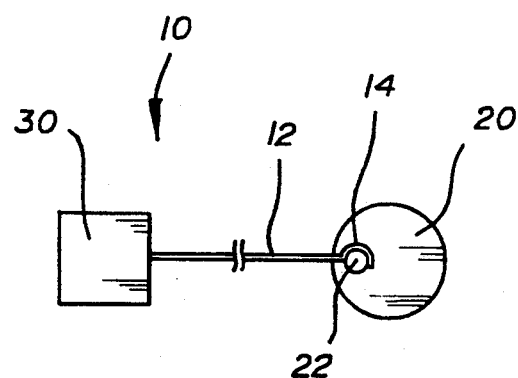
FIG. 1 is a top view of a conventional (prior art) electrode connector as it interconnects a stud-containing electrode and a monitor.
Figure 2:
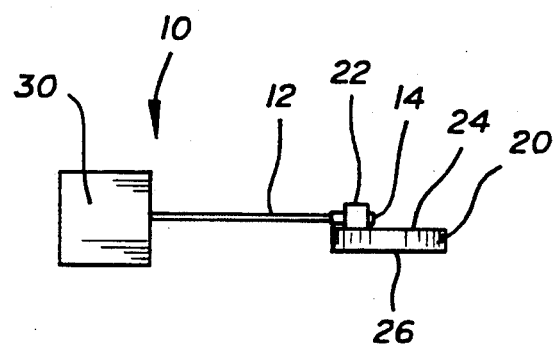
FIG. 2 is a side view of a conventional (prior art) electrode connector as it interconnects a stud-containing electrode and a monitor.

FIGS. 1 and 2 show a conventional (prior art) electrode connector assembly 10 as it interconnects a stud-containing electrode 20 and a monitor 30. Conventional assembly 10 includes a lead wire 12 and a female couple 14. Electrode 20 has a male stud 22 projecting from its upper surface 24 and is typically both metal and relatively large.

In use, electrode 20 is affixed to the skin of the patient to be monitored so that the lower surface 26 of electrode 20 contacts the skin and stud 22 projects away from the skin. One reason explaining why stud-containing electrodes remain in frequent use is that, historically, that type of electrode has gained widespread acceptance. Another reason is that the stud provides affirmative assurance during engagement that electrical connection has been attained. A third reason is that the stud facilitates rotation and, consequently, helps to promote patient comfort and to assure continual electrical connection. Finally, conventional electrode connector assemblies such as assembly 10, which are suited for connection to the stud-containing electrodes, are already in place.

Conversion away from the stud-containing electrodes would require hospitals and clinics to discard peripheral equipment such as the existing electrode connectors. Moreover, during transition away from the stud-containing electrodes and toward studless electrodes, problems would arise because the existing peripheral equipment is not compatible with both types of electrodes. For these and other reasons, conversion has been avoided and stud-containing electrodes remain in widespread use.

Female couple 14 of conventional electrode connector assembly 10 is adapted to engage electrically stud 22 of electrode 20. Lead wire 12 of assembly 10 is connected at one end to female couple 14 and at its opposite end to monitor 30.

In operation, electrical signals generated by or transmitted to monitor 30 travel along lead wire 12 to or from female couple 14. The electrical contact between lead wire 12 and stud 22 allows the signals to enter or exit stud-containing electrode 20. Then, in turn, the signals are applied to or measured from the skin through the contact between bottom surface 26 of electrode 20 and the skin.

As discussed above, stud-containing electrodes like electrode 20 are relatively expensive to manufacture and use. Consequently, a thin, lightweight, flexible, convenient, and disposable electrode was developed which alleviates many of those disadvantages. The electrode is sufficiently inexpensive to manufacture that it is practical to discard the electrode after only one use. The electrode is easy and quick to apply, deformable for application on almost any part of the skin, compact and easy to use and store, and provides good electrical contact to the skin. Moreover, the electrode does not have a stud.

Figure 5:
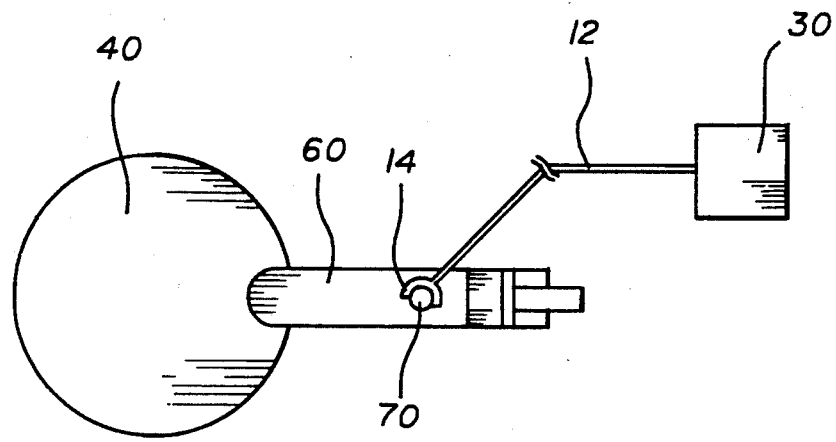
FIG. 5 is a top view of the electrode connector of FIGS. 3 and 4 shown in electrical contact with a tab-type electrode and the conventional connector of FIGS. 1 and 2.
Figure 6:
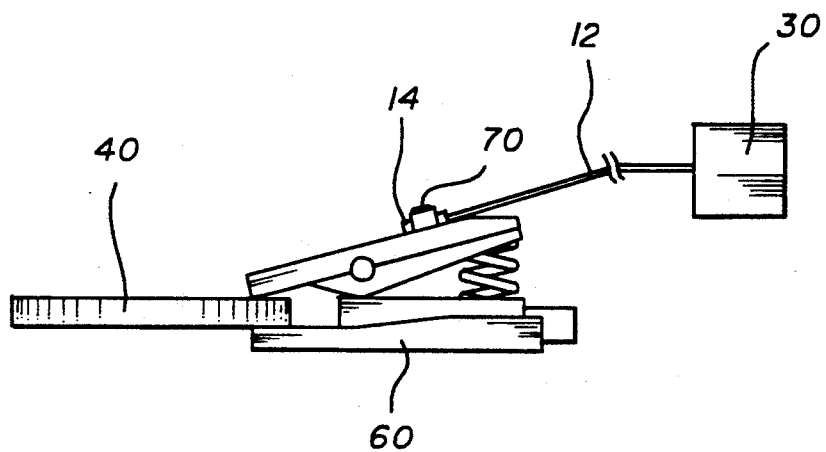
FIG. 6 is a side view of the electrode connector of FIGS. 3 and 4 shown in electrical contact with a tab-type electrode and the conventional connector of FIGS. 1 and 2.

Such a studless electrode is shown as electrode 40 in FIGS. 5 and 6. (Note that like reference numerals have been used throughout the various figures of the drawing to identify like elements.) Electrode 40 usually has a flexible backing including an upper electrically insulating layer, such as a thin sheet of vinyl plastic, and an electrically conductive layer. To the lower surface of the conductive layer is laminated a flexible layer of an electrically conductive gel matrix which, during use, makes electrical contact with the skin of the patient. The matrix, usually sticky, is covered before use by a removable release liner. A lateral extension or tab may be provided to extend the backing and provide a contact area to facilitate connection with an associated electrode connector.

Standard, conventional, lead wire plus female couple assemblies 10 cannot engage electrode 40. There is no stud on electrode 40 to engage female couple 14. The present invention allows conventional assemblies 10 to engage electrode 40 and, therefore, hospitals and clinics can realize the benefits of using electrode 40 without sacrificing their continued ability to use electrode 20 if a patient arrives with such an electrode in place.

Figure 3:
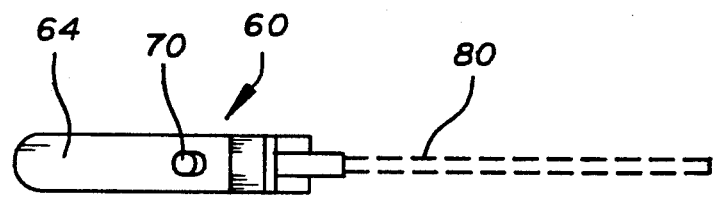
FIG. 3 is a top view of an electrode connector according to the present invention.
Figure 4:
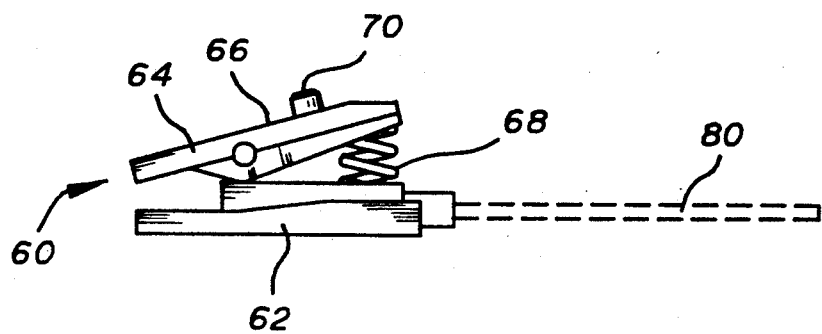
FIG. 4 is a side view of an electrode connector according to the present invention.

FIGS. 3 and 4 illustrate the adaptive electrical connector of the present invention. The connector includes means for electrically and mechanically securing the connector to electrode 40—even though electrode 40 does not have a male stud. A variety of means are available to perform that function. One means is a variation of the standard electrical alligator clip 60, as shown in FIGS. 3-6.

Clip 60 in essence is an industrial alligator clip with a heat-shrunk plastic sheath extending over a majority of the portion of the clip member. A base 62, a top 64, and a spring 68 disposed between base 62 and top 64 form two, pivotally mounted, spring-biased jaws which grasp the contact portion of electrode 40. Base 62 and top 64 may have multiple teeth for gripping the electrode.

Various alternative means are available, as would be known to a person of ordinary skill in the art, to electrically and mechanically secure the connector to electrode 40. Such means include those disclosed, for example, in U.S. Pat. No. 4,702,256 issued to Robinson et al.; U.S. Pat. No. 4,797,125 issued to Malana; and U.S. Pat. No. 4,178,052 issued to Ekbom et al. Clip 60 is shown by way of example; the securing means of the present invention is not intended to be limited to clip 60.

Clip 60 is an important component for monitoring patients with high accuracy. As an important component, clip 60 must have excellent corrosion resistance and chemical stability because it will often contact various chemicals, likely to attack it, during use in medical institutions. Clip 60 must also provide a link of low electrical resistance between electrode 40 and female couple 14 and, ultimately, monitor 30. That link should be a good electrical conductor in order to carry even a weak electrical current to or away from the skin.

One component of that link is a stud 70. Top 64 of clip 60 has a top surface 66. Stud 70 is formed on top surface 66 to provide easy access to stud 70 by female couple 14. Preferably, stud 70 is integrally formed on top surface 66 by molding, welding, soldering, or the like.

Stud 70 projects above top surface 66 of top 64 of clip 60. Consequently, it is subject to the risk of damage by hitting other objects during use and storage. In addition, the electrical contact between stud 70 and female couple 14 is essential; that contact should be protected from disengagement. It is preferable, therefore, that stud 70 be located on top surface 66 in the approximate center of top surface 66. Such a location offers added strength to stud 70 and protection to the contact between stud 70 and female couple 14.

In other respects, stud 70 is a standard stud, like stud 22 on electrode 20, able to connect with a standard female couple, like couple 14. Such studs are usually formed from a metal to assure electrical conductivity between the electrode and the female couple.

It may be important in some applications, however, to provide a clip 60 (including stud 70) which is x-ray transparent, as defined in U.S. Pat. No. 4,685,467 issued to Cartmell et al. Other procedures, such as nuclear magnetic resonance (NMR), tolerate only minimal amounts of metal in an electrode and connector assembly. Accordingly, clip 60 and stud 70 may be molded together using, for example, a carbon-filled plastic material.

Rotational movement between female couple 14 and stud 70 may be necessary either to maintain a good electrical connection between electrode 40 and monitor 30 or to ensure patient comfort. Such movement is especially necessary when the patient stirs. By placing stud 70 on clip 60, significant rotational motion of the connector relative to the electrode is assured.

An advantage of the invention is that it is adapted to engage a standard female couple having a lead wire. As shown in FIGS. 5 and 6, female couple 14 simply hooks or snaps onto stud 70 of clip 60. This allows the system to be adaptable; the standard female couple 14 and lead wire 12 can be unhooked or unsnapped from stud 70 on clip 60, then hooked or snapped onto stud 22 of stud-containing electrode 20—and vice versa. This is important especially when a patient arrives with electrodes already in place. Another advantage is the affirmative feel or sound consequent upon hooking or snapping female couple 14 onto stud 70; the operator is assured that electrical connection has been achieved.

It is also possible to electrically connect clip 60 directly to monitor 30. For that purpose, a lead cable 80 (shown by the phantom lines in FIGS. 3 and 4) may be electrically connected, as is known in the art, to clip 60. Cable 80 will have a plug, on its end opposite connection to clip 60, able to engage monitor 30. Thus, if a hospital or clinic were to use only studless electrodes like electrode 40 and, therefore, never required adaption to stud-containing electrode 20, it might use clip 60 with cable 80.

The invention is convenient to use and allows a conventional lead plus female couple to be connected to both stud-containing and studless tab electrodes. Because it provides a secure connection to a tab-type electrode, the invention permits the less expensive tab-type electrodes to be used in a variety of circumstances where before only the stud-containing electrodes could be used. Moreover, the present invention increases flexibility: either the stud-containing or tab electrodes can be used with the same, conventional, lead plus female couple. The design of the invention is uncomplicated, avoiding unnecessary elements which might obstruct operation in the wide variety of circumstances in which the invention must function. The design is also rugged in construction and reliable in operation.

Although the invention is illustrated and described herein as embodied in an adaptive medical electrode connector which can be (1) electrically and mechanically secured to a studless electrode affixed on the skin of a patient and (2) electrically engaged through a male stud integrally formed with and projecting from the connector to a monitor having a lead wire plus female couple assembly, for electrically interconnecting the electrode and monitor, the invention is nevertheless not intended to be limited to the details shown. Rather, various modifications may be made in the details within the scope and range of equivalents of the claims and without departing from the spirit of the invention.

What is claimed is:

1. A disposable medical electrode connector for releasably and electrically connecting either (a) a thin, flexible, disposable, studless, tab-type medical electrode or (b) a medical electrode having a male stud, the electrode secured on the skin of a patient, to a monitor either through a lead cable or through a conventional female couple and lead wire assembly, said disposable medical electrode connector being entirely separate from the electrode, connected to the electrode and not the patient, and comprising:
   a base having an electrically conducting portion;
   a top having a top surface and an electrically conducting portion facing said electrically conducting portion of said base;
   means disposed between said base and said top for mechanically forcing said electrically conducting portion of said base toward said electrically conducting portion of said top to mechanically and electrically engage, between said electrically conducting portion of said base and said electrically conducting portion of said top, either the tab of a tab-type medical electrode or the male stud of a medical electrode having a male stud;
   means for electrically connecting a lead cable to said electrically conducting portion of said base, the lead cable being attached to a monitor; and
   a male stud electrically connected to said electrically conducting portion of said top and integrally formed with and projecting from said top surface of said top for mechanically and electrically engaging a conventional female couple and lead wire assembly, said assembly being attached to said monitor.

2. An electrode connector as claimed in claim 1 wherein said base, said top, and said forcing means from an alligator clip.

3. An electrode connector as claimed in claim 1 wherein said male stud is molded to said securing means.

4. An electrode connector as claimed in claim 1 wherein said male stud is welded to said securing means.

5. An electrode connector as claimed in claim 1 wherein said male stud is soldered to said securing means.

6. An electrode connector as claimed in claim 1 wherein said male stud is formed on said top surface of said top in the approximate center of said top surface.

* * * * *